United States Patent
Kroll et al.

(10) Patent No.: US 7,177,684 B1
(45) Date of Patent: Feb. 13, 2007

(54) ACTIVITY MONITOR AND SIX-MINUTE WALK TEST FOR DEPRESSION AND CHF PATIENTS

(75) Inventors: Mark W. Kroll, Simi Valley, CA (US); Bruce Kleine, Reseda, CA (US)

(73) Assignee: Pacesetter, Inc., Sylmar, CA (US)

( * ) Notice: Subject to any disclaimer, the term of this patent is extended or adjusted under 35 U.S.C. 154(b) by 484 days.

(21) Appl. No.: 10/613,136

(22) Filed: Jul. 3, 2003

(51) Int. Cl.
*A61B 5/11* (2006.01)

(52) U.S. Cl. .......................... 607/17; 607/19; 600/595

(58) Field of Classification Search ............ 607/17–19; 600/510, 513, 595; 604/66
See application file for complete search history.

(56) References Cited

U.S. PATENT DOCUMENTS

| | | | | |
|---|---|---|---|---|
| 4,659,077 A | * | 4/1987 | Stropkay | 482/70 |
| 5,549,652 A | * | 8/1996 | McClure et al. | 607/28 |
| 5,978,713 A | * | 11/1999 | Prutchi et al. | 607/60 |
| 6,045,513 A | | 4/2000 | Stone et al. | 600/508 |
| 6,102,874 A | | 8/2000 | Stone et al. | 600/595 |
| 6,190,324 B1 | | 2/2001 | Kieval et al. | 600/483 |
| 6,280,409 B1 | * | 8/2001 | Stone et al. | 604/67 |
| 6,625,493 B2 | * | 9/2003 | Kroll et al. | 607/17 |
| 2002/0138213 A1 | * | 9/2002 | Mault | 702/32 |

FOREIGN PATENT DOCUMENTS

WO    WO 99/58056    11/1999

* cited by examiner

*Primary Examiner*—Robert E. Pezzuto
*Assistant Examiner*—Eric D. Bertram

(57) ABSTRACT

An implantable device that can automatically monitor and record patient activity as sensed by an activity monitor. In certain variations, the activity monitor can include an accelerometer providing three-axis acceleration signals and in other variations the activity sensor can include a position sensor, such as a GPS receiver. The implantable device automatically determines if patient activity exceeds a determined threshold and monitors and records a total equivalent distance traveled for a determined period, which may be set equal to a standard measure such as a six minute period. The device can monitor and record multiple periods of activity and the periods may be consecutive, overlapping, and/or separate in time. The device may store all activity records or selected records which may correspond to daily, weekly, or other periodic maxima.

29 Claims, 11 Drawing Sheets

| Date | Max. Count for Det. Period | Equiv. Dist. |
|---|---|---|
| mm/dd/yy | 552 | 243 m |
| mm/dd/yy | 548 | 241 m |
| mm/dd/yy | 530 | 233 m |
| mm/dd/yy | N.R. | 0 m |
| mm/dd/yy | 550 | 242 m |
| mm/dd/yy | 548 | 241 m |
| mm/dd/yy | 557 | 245 m |
| mm/dd/yy | 553 | 243 m |
| mm/dd/yy | 541 | 238 m |
| mm/dd/yy | 550 | 242 m |

| Date | Max. Count for Det. Period | Equiv. Dist. |
|---|---|---|
| mm/dd/yy | 552 | 243 m |
| mm/dd/yy | 548 | 241 m |
| mm/dd/yy | 530 | 233 m |
| mm/dd/yy | N.R. | 0 m |
| mm/dd/yy | 550 | 242 m |
| mm/dd/yy | 548 | 241 m |
| mm/dd/yy | 557 | 245 m |
| mm/dd/yy | 553 | 243 m |
| mm/dd/yy | 541 | 238 m |
| mm/dd/yy | 550 | 242 m |

Fig. 9c

ACTIVITY MONITOR AND SIX-MINUTE WALK TEST FOR DEPRESSION AND CHF PATIENTS

FIELD OF THE INVENTION

The invention relates to the field of implantable medical devices and, in particular, to an implantable device that automatically monitors a patient's activity level, determines peak physical output levels, and provides this information to a clinician for evaluation with respect to the patient's physical and mental status.

BACKGROUND OF THE INVENTION

Exercise capacity and natural frequency of occurrence and intensity is a reliable indicator of a person's mental and physical health status. A person of good physical and mental health will tend to regularly undertake physically taxing exertion either through dedicated exercise or through the course of their normal daily and recreational activities. The intensity and duration of the physical exertion is a good indicator of their overall physical health and the frequency with which it occurs is indicative of their mental health and attitude.

Conversely, a reduced level and/or capacity for exercise is correlated with a state of reduced mental and/or physical health. A state of depression, for example, is positively correlated with a reduced frequency and duration of physical exertion. A person suffering from depression will typically reduce the level of physical exertion they undertake to maintain a home, for example, and will typically exhibit a general lethargy and increased sedentary behavior. A person suffering from depression will also often avoid dedicated exercise.

A person suffering an acute or chronic physical impairment, such as a survivor of a myocardial infarction (MI) or a person with congestive heart failure (CHF) will typically have a reduced capacity for exercise. The limited cardiovascular output of such persons limits the ability they have to engage in physically strenuous exercise. It is often the case that a person suffering a serious physical malady, such as MI or CHF, will also exhibit some depression symptoms further reducing their exercise level.

Thus, natural exercise frequency and intensity can be used as a general diagnostic for the physical and mental condition of a patient. Changes in the level and duration of exertion of which they are capable is also highly indicative of the progression of a condition, such as CHF, and is useful as an adjunct to other physiological measurements. It also provides valuable clinical feedback on the efficacy of treatment regimens.

FIG. 1 shows some general interactions and contributing factors to depression and some typical consequences thereof. Depression is often treated with tricyclic antidepressants. Common side-effects of the tricyclics is a decrease in heart rate variability and an orthostatic hypotension condition in the medicated patient. A decreased heart rate variability often leads to a decreased vagal tone which is an indicator for ventricular tachycardia/fibrillation (VT/VF). As potentially lethal conditions, an increased risk of VT or VF leads to an increased mortality which typically causes increased anxiety in a patient aware of their condition. Increased anxiety tends to exacerbate depression thus forming a potential reinforcing cycle.

Depression also tends to lead to an exaggerated orthostatic response as well as decreased vagal tone and increased sympathetic tone. Decreased vagal tone and increased sympathetic tone also are indicators for increased VT and VF susceptibility, which as previously mentioned, leads to an increased mortality which can increase anxiety and the depressive condition and another potential reinforcement cycle.

As previously mentioned, depression tends to lead to a lower level of exercise and also a reduced compliance with following a medication regimen. Depression also tends to lead to an increase in aggragability of blood platelets. All three of these factors are risk factors for myocardial infarction. As previously mentioned, occurrence of an MI can lead to a CHF condition. CHF is also an indicator for increased mortality and another possible feedback path for a reinforced cycle of increased depression.

Thus, it can be understood that effectively treating a patient's depression and any underlying medical condition is important in securing the patient's overall health. Evaluating the patient's capacity for exercise can provide valuable information regarding the patient's current status and the effectiveness of treatment regimens. One widely used standard measure of a person's exercise capacity is a six-minute walk test. The six-minute walk test is generally performed on a stationary treadmill and measures the effective distance that a patient is able to walk in a six-minute period. The six-minute walk test is performed under standardized conditions and provides a repeatable, commonly accepted standard measurement tool.

A practical diagnostic drawback with this method of determining the patients condition is that it can require a stationary treadmill implement. This aspect is disadvantageous as it requires either installation of treadmill equipment at a patient's home for self-testing or a trip to a clinical setting equipped with a treadmill. The test can be administered as a true measure of actual distance traveled by walking, however this aspect introduces the difficulty of accurately determining the actual distance walked. Further, the six-minute walk test as typically administered is not a measure of the natural occurrence of a patient's exercise, but rather a measure taken under artificial conditions. Patient surveys can be administered to solicit information about their normal, natural activities, however, as is known in the art, self-surveys can be inaccurate particularly, if the patient is not performing exercise as requested by their physician.

Thus, it would be desirable to have a convenient, unobtrusive method of determining a patient's capacity for and natural frequency of taxing exercise. It would be advantageous to be able to gather the information in an invisible manner from the patient's perspective, e.g. without patient input or interaction, so as to reduce the patient's conscious awareness of the data gathering and thus reducing artificial impact on their natural tendencies. It would also be advantageous to gather information over an extended period of time so as to track the progression of a patient's condition over time. It would also be beneficial to automatically evaluate the patient's natural exercise activity in an equivalent to a clinical six-minute walk test to allow comparison to a standard measure.

SUMMARY

The above referenced needs are satisfied by an implantable device for automatically monitoring and reporting patient physical activity. The implantable device is comprised of at least one sensor ("the sensor") providing information related to patient movement, a processor in communication with the sensor wherein the processor evaluates the information provided by the sensor, automatically determines when the sensor is indicating patient movement in excess of a threshold value, and automatically determines a maximum equivalent quantified activity during a determined interval, memory in communication with the sensor so as to receive and store data related to the patient's movement, and a telemetry circuit in communication with the memory such that the device can selectively report stored data related to the patient's activity by telemetrically transmitting such data.

The sensor can comprise an accelerometer or a position sensor, such as a global positioning system receiver. Automatically determining when the sensor is indicating patient movement in excess of a threshold value can comprise establishing a cyclical acceleration in excess of a threshold value indicative of patient walking.

Determining the maximum equivalent quantified activity during the determined period can comprise determining a maximum equivalent distance walked, which can comprise periodically incrementing an initial distance value with a determined equivalent distance traveled during a measurement period. The equivalent distance traveled during the measurement period may be determined as the double integral of an acceleration value over time for the measurement period.

The determined interval may be selected to correspond to a standard clinical measurement period. The device may also further comprise a stimulation circuit adapted to provide therapeutic electrical stimulation and a controller in communication with the sensor and the stimulation circuit such that upon detection of a cardiac arrhythmia as sensed by the sensor, the controller can induce the stimulation circuit to deliver a therapeutic stimulation.

Another embodiment described herein is directed to a method of automatically determining indices of a patient's physical activity and reporting the same with an implantable device. The method comprises measuring a parameter indicative of patient movement, determining whether the measurement of patient movement exceeds a threshold indicating patient movement of sufficient intensity and duration to indicate further evaluation, calculating an equivalent exertion index for a determined interval, recording at least one equivalent exertion index, and providing the at least one equivalent exertion index to an external device.

Measuring the parameter indicative of patient movement can comprise measuring an acceleration and/or measuring patient position in space with respect to time.

Determining whether the measurement of patient movement exceeds a threshold indicating patient movement of sufficient intensity and duration to indicate further evaluation can comprise evaluating whether the measurement of patient movement is indicative of the patient walking.

Calculating an equivalent exertion index for a determined interval can comprise calculating an equivalent distance walked during the determined interval, which may comprise a six minute interval.

Calculating an equivalent exertion index for a determined interval can comprise periodically incrementing an equivalent distance walked for the duration of the determined interval.

Recording at least one equivalent exertion index can comprise recording the highest equivalent exertion index yet calculated and/or the highest exertion index measured during a given period, such as a week.

Providing the at least one equivalent exertion index to an external device can comprise telemetrically transmitting the recorded equivalent exertion index to a physician programmer.

Yet another aspect of the invention is a system for automatically monitoring patient physical activity and for evaluating the same, the system comprising an implantable device comprising means for sensing information related to patient movement, processing means in communication with the sensing means wherein the processing means evaluates information provided by the sensing means, automatically determines patient movement in excess of a threshold value, and automatically determines a maximum equivalent quantified activity during a determined interval, and data storage means in communication with the processing means so as to receive and store data related to the patient's movement and store data related to the maximum equivalent quantified activity determined over time, an external device comprising display means for display of information received from the implantable device, and telemetry means providing communication between the implantable device and the external device such that the data stored in the implantable device may be selectively transmitted to the external device for display and evaluation by a user.

The sensing means can comprise an accelerometer and/or the external device can comprise a physician programmer.

The implantable device may further comprise stimulation means adapted to selectively provide therapeutic electrical stimulation and control means in communication with the sensing means and the stimulation means such that upon detection of a cardiac arrhythmia as sensed by the sensing means, the control means can induce the stimulation means to deliver a therapeutic stimulation. These and other objects and advantages of the invention will be more apparent from the following description taken in conjunction with the accompanying drawings.

BRIEF DESCRIPTION OF THE DRAWINGS

FIG. 9c indicates an example of a record of patient activity that can be accessed for evaluation of the patient's past activity.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
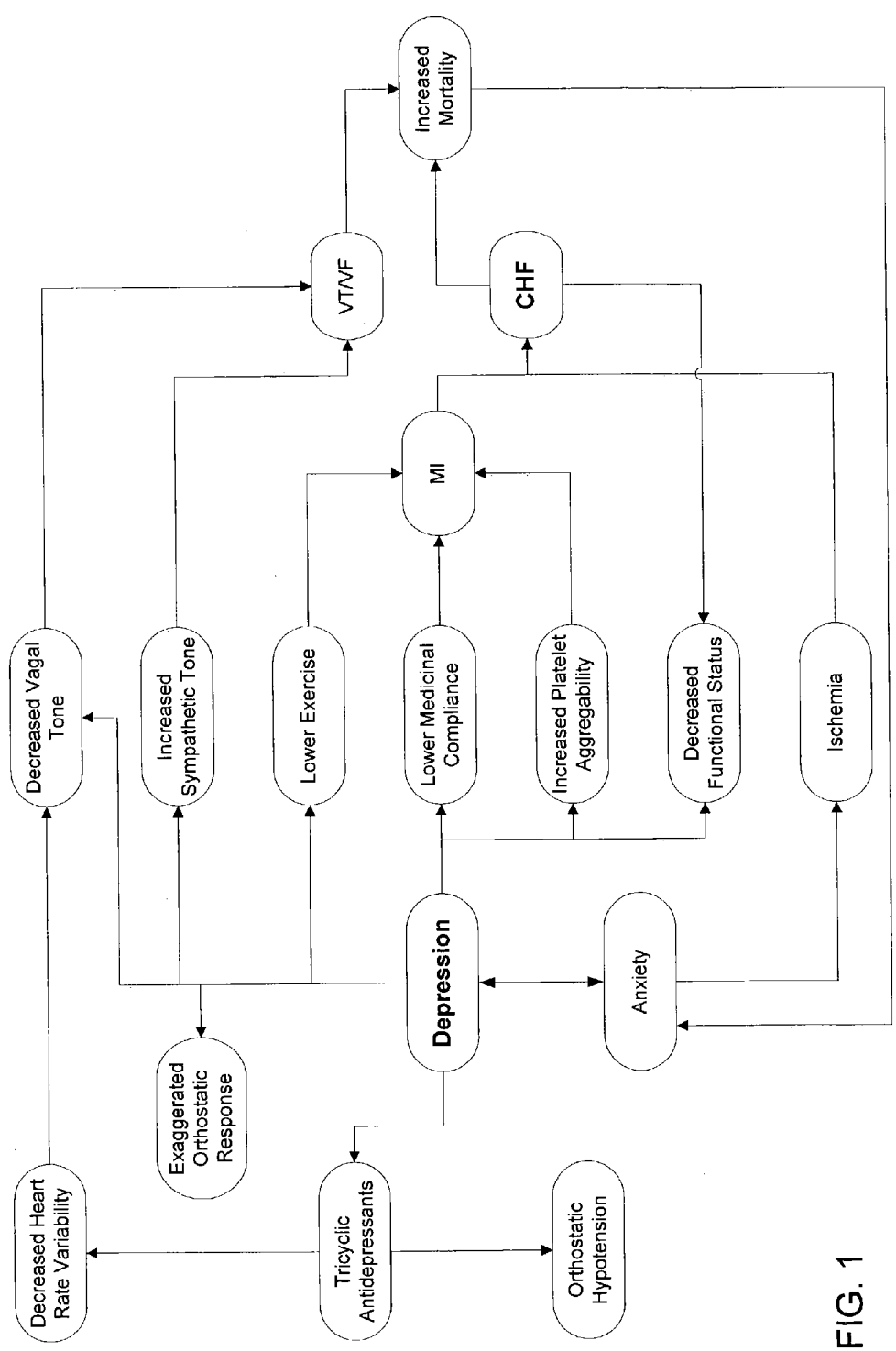
FIG. 1 is a diagram of some indicators and common subsequences of depression and medical conditions, such as MI and CHF.
Figure 2:
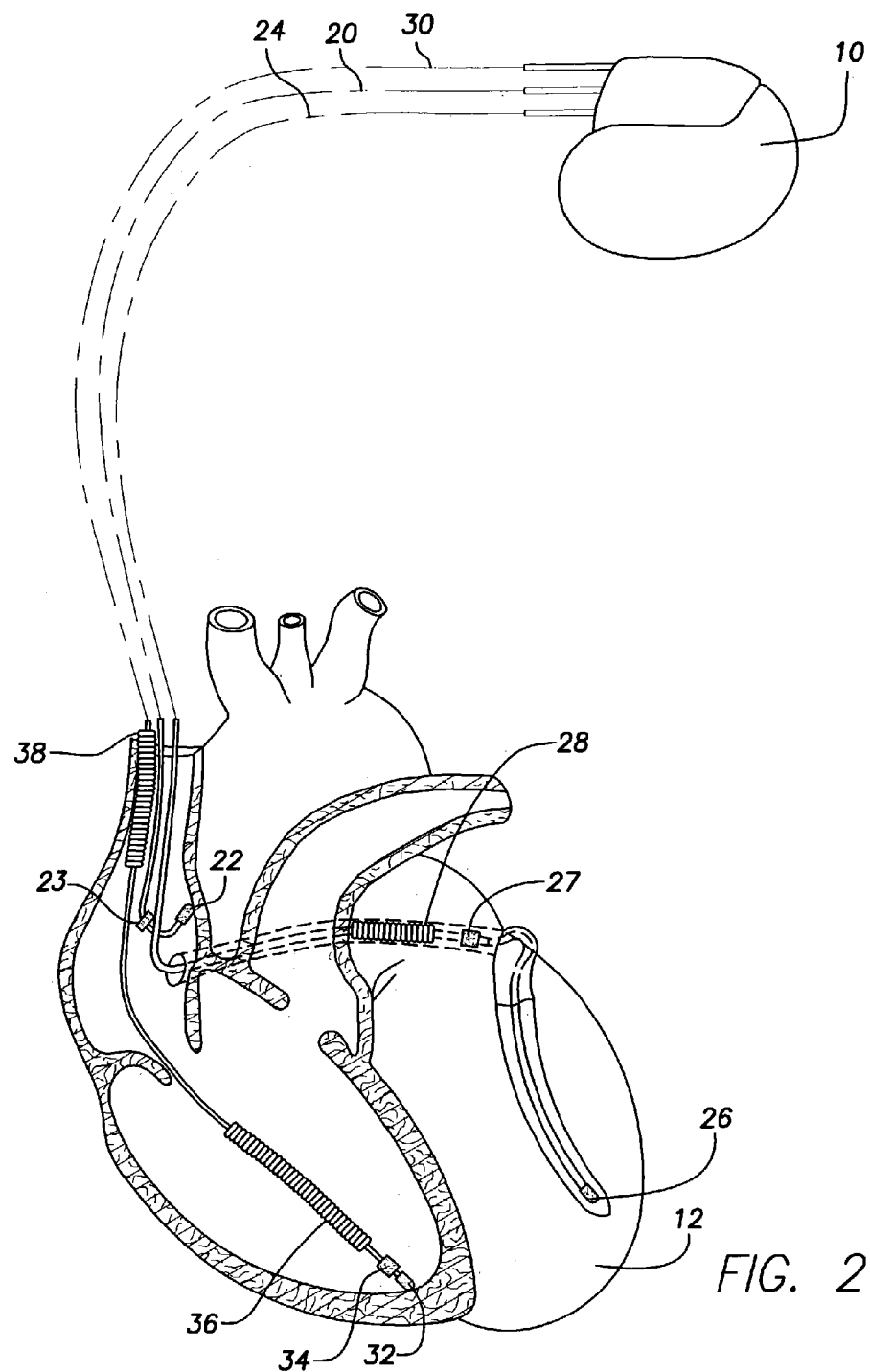
FIG. 2 is a simplified diagram illustrating an implantable stimulation device in electrical communication with at least three leads implanted into a patient's heart for delivering multi-chamber stimulation and shock therapy.

As shown in FIG. 2, there is one embodiment of a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 3:
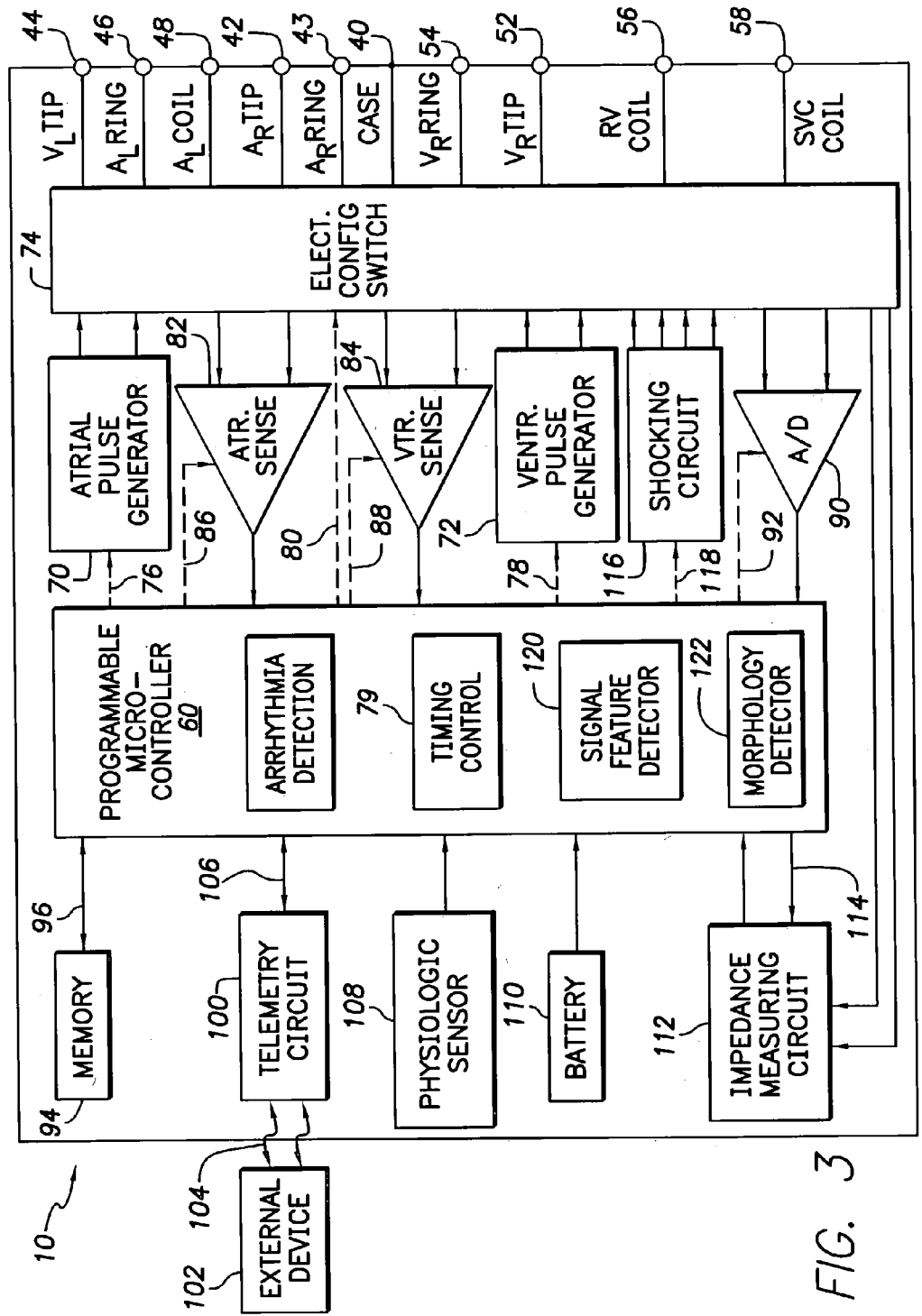
FIG. 3 is a functional block diagram of a multi-chamber implantable stimulation device illustrating the basic elements of a stimulation device which can provide cardioversion, defibrillation and pacing stimulation in four chambers of the heart.

As illustrated in FIG. 3, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, desired operating parameters or other programming instructions of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 may be activated from a standby condition in response to an indication from a radio frequency (RF) detector (not shown) that signals of a predetermined strength are being received. The telemetry circuit 100 can communicate with the microcontroller 60 via a communication link 106.

The telemetry circuit 100 also advantageously allows intracardiac electrograms and status information relating to the operation of the device 10 (as contained in the microcontroller 60 or memory 94) to be sent to the external device 102 through an established communication link 104.

FIG. 3 also shows at least one implantable sensor 108 in communication with the device 10. The at least one sensor 108 internally monitors parameters of clinical interest relating to patient condition. In various embodiments of the invention, the sensor 108 can provide information relating to respiration rate and/or tidal volume, arterial and/or venous $O_2$ saturation, heart stroke volume, temperature, patient orientation and/or movement, and hemodynamic status such as pressure. FIG. 3 illustrates the sensor 108 as being located inside the device 10, however, it will be understood that in alternative embodiments the sensor 108 can be co-located with the device 10, but externally positioned thereto or positioned separate from the device 10. The exact placement or location of at least one sensor 108 can vary in different embodiments without detracting from the scope of the invention. It will also be understood that the communication between the sensor 108 and the device 10 can include wired or wireless communication in various embodiments.

The at least one physiologic sensor 108 is commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. It is also to be understood, that in certain embodiments, the sensor 108 is capable of sensing multiple parameters and providing all the sensed parameters or a selected number of the parameters to the device 10.

The sensor 108 also provides information related to patient movement. In certain embodiments, the sensor 108 provides acceleration information, such as from a three-axis accelerometer. Information from the sensor 108 comprising a 3-D accelerometer can provide acceleration signals resolved into three orthogonal directions, commonly referred to as x, y, and z axes and this information may be constantly variable or periodically updated. In embodiments where the sensor provides constantly variable information, it may be considered that, for short intervals of time, the acceleration may be considered a constant.

In other embodiments, the sensor 108 can comprise a position sensor, such as a global positioning system (GPS) receiver. In these embodiments, the sensor 108 provides information indicating the patient's position in space. From this can be derived information related to the patient's movement over time. In particular embodiments, the sensor 108 can directly provide the device 10 with information related to the patient's movement, such as distance traveled from a starting point, instantaneous and average velocities, etc.

The stimulation device additionally includes a battery 150 which provides operating power to all of the circuits shown in FIG. 3. For the stimulation device 10, which employs shocking therapy, the battery 150 must be capable of operating at low current drains for long periods of time, and then be capable of providing high-current pulses (for capacitor charging) when the patient requires a shock pulse. The battery 150 must also have a predictable discharge characteristic so that elective replacement time can be detected.

As further shown in FIG. 3, the device 10 is shown as having an impedance measuring circuit 152 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In FIGS. 4–9a, flow charts are shown describing overviews of the operation and novel features implemented in embodiments of the device 10. It should be understood that the actions performed as indicated in FIGS. 4–9a and described in greater detail below are partially performed by the implantable device 10. In these flow charts, the various algorithmic steps are summarized in individual "blocks". Such blocks describe specific actions or decisions that are made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Figure 4:
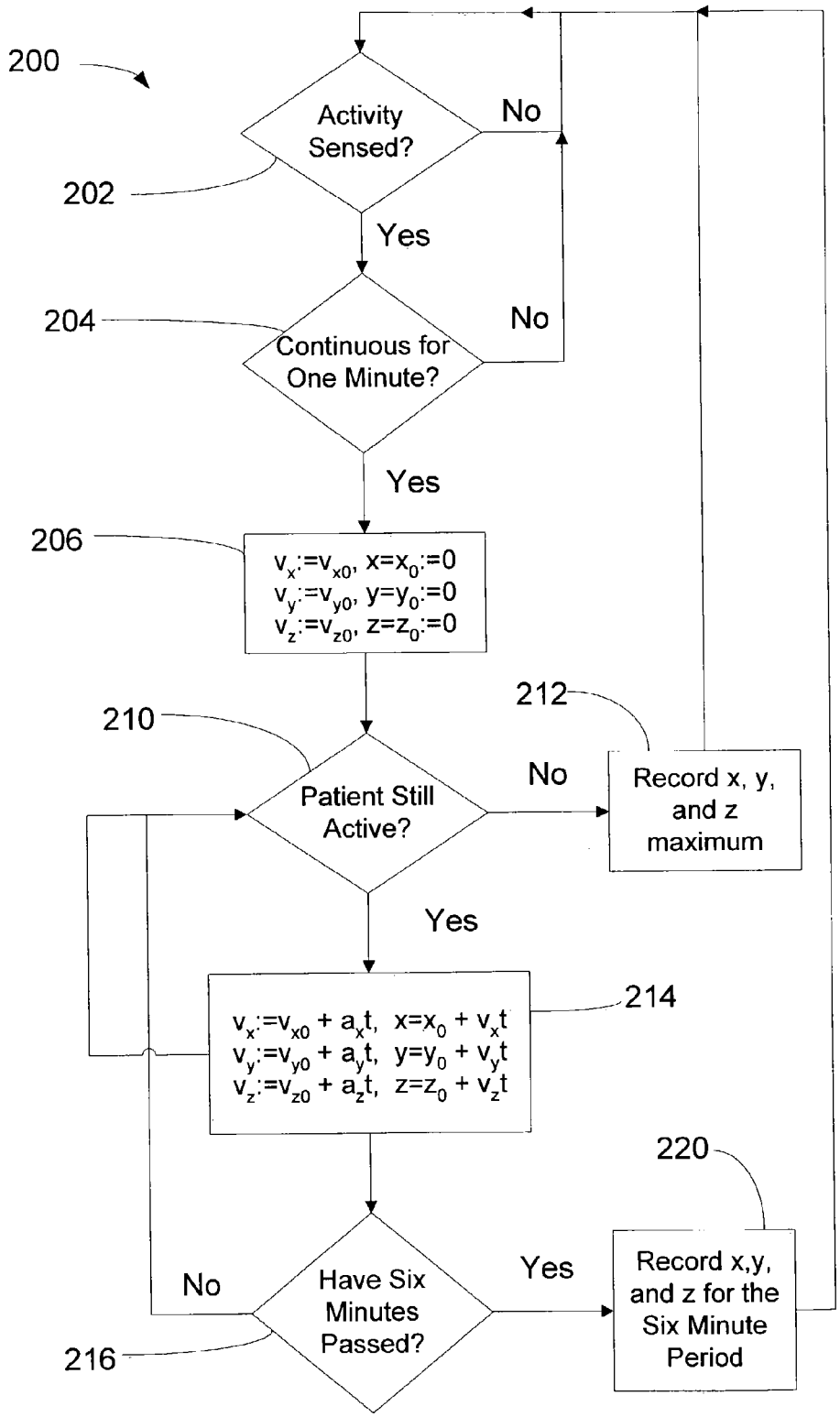
FIG. 4 is a flow chart of an embodiment of a method of automatically determining patient activity suitable for use with the device of FIGS. 2 and 3 where an acceleration signal is provided.

FIG. 4 illustrates one embodiment of a process 200 for automatically determining patient activity where the sensor 108 provides an acceleration signal. In the embodiments of the invention to be described, it is to be assumed that the device 10 is generally performing other operations as previously described in parallel to the operation of the invention as described herein. Further, in the embodiment described herein, the determination of patient activity is initiated automatically by the device 10 however, in alternative embodiments, the initiation of determination of patient activity can be triggered by a control signal such as from a telemetrically provided control signal or other user input.

In an ongoing decision state 202 an evaluation is made of whether patient activity has been sensed. In this embodiment an affirmative result of this decision would result when signals from the sensor 108, in this embodiment comprising an acceleration, have exceeded a threshold value. The threshold determination can comprise evaluating an acceleration magnitude indicating a change to physical activity from a sedentary or rest condition of the patient and/or a determination of cyclic acceleration indicating, for example, the oscillatory movement of walking. A negative result of the decision state 202 results in continued monitoring for patient activity. A positive result of decision state 202 leads to a decision state 204 wherein a determination is made whether the activity has continued for one minute. A no result of decision state 204 results in continued monitoring for renewed activity in state 202. State 204 provides the ability to determine whether an acceleration signal is of short duration, such as, for example a brief period of activity such as getting up to retrieve a book and a subsequent return to a seated position for reading.

A positive result of state 204 indicates a possibility that the physical activity is of an ongoing nature, in which case such activity will be recorded and analyzed in greater detail beginning in state 206. In state 206 initial position values in x, y, and z coordinates are set to an initial state and, in this embodiment, set to zero to indicate the beginning of the patient's activity and to simplify the determination of a total distance traveled. Initial values for velocity may also be set to initial values determined from a typical speed corresponding to normal patient activity, such as an average walking speed determined on a treadmill in a clinical evaluation of the patient. Following this, a decision state 210 determines whether patient activity is continuous. The determination of state 210 can be made by confirmation of an oscillating acceleration signal, such as along one or more of the axes, such as the z axis, indicating the cyclical acceleration of walking. A negative result of decision state 210 would indicate that, while the patient's activity exceeded, in this embodiment, one minute, the activity was not of sufficient duration to constitute exercise or other physical activity which the device 210 would store for further analysis. A positive result of decision state 210 would indicate that the patient activity is ongoing and will be analyzed and recorded as indicated as follows.

In state 210, velocity values along the x, y, and z coordinates are established in an iterative manner such that a new velocity value is set equal to the previous, or initial velocity value and incremented by the product of the acceleration value along the respective axis multiplied by the time interval. The particular time interval is not crucial to the invention, however, it would be generally preferred that the selected time period t correspond generally to an update or a refresh period of the sensor 108 providing, in this embodiment, an acceleration signal. The position values along the x, y, and z coordinates are updated in a similar manner wherein the initial positions $x_0$, $y_0$, $z_0$ are incremented by the product of the velocity components along the x, y, and z axes multiplied by the time period t.

Following the update of the velocity and position values in state 210, a decision is made in state 216 whether the duration of the patient activity has exceeded a predetermined period which, in this embodiment, is six minutes to correspond to the standard six minute walk test. A negative result of the decision of state 216 will result in a return to state 210 wherein it is established whether the patient activity is continuing and again a positive result of decision state 210 will result in an updating and incrementing of the velocity and position values in state 214 as previously described. Thus, in this embodiment of the invention, a stepwise integration is made of the acceleration signals provided by the sensor 108 to provide stepwise integrated velocity and position values.

If the result of decision state 216 returns a positive result, the present x, y, and z values are recorded to correspond to the approximate total distance traveled by along the x, y, and z axes from the initial position established in state 206. This recordation occurs in state 220. Following the recordation in state 220 a return is made to the decision state of 202 wherein a determination is made whether patient activity is being sensed. Thus, in this embodiment it is foreseeable that multiple six minute periods of activity can be recorded in state 320.

In various embodiments, the device 10 may make an evaluation of the records in state 220 for comparison and may store only the greatest distance as determined by the x, y, and z values for a particular period as stored in states 220. The device 10 may store a complete record of all six minute periods recorded in state 220, only the greatest distance traveled on a daily, monthly, or other period, and/or only the single greatest distance record in state 220 over a longer duration.

Figure 5:
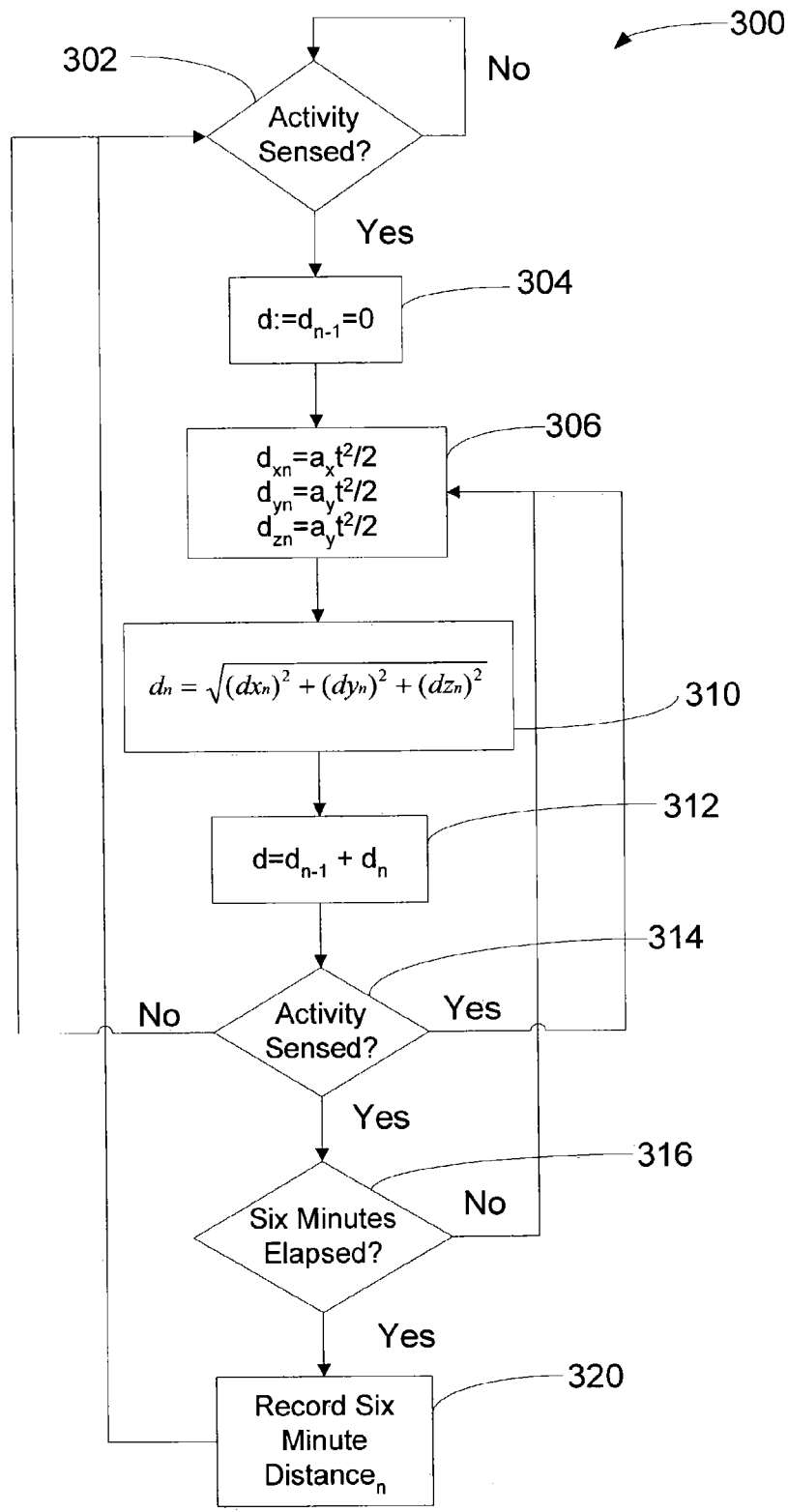
FIG. 5 is a flow chart of an alternative embodiment of a method of automatically determining patient activity suitable for use with the device of FIGS. 2 and 3 where an acceleration signal is provided.

FIG. 5 illustrates an alternative embodiment of the invention adapted for applications where the sensor 108 provides an acceleration signal along x, y, and z axes. In this embodiment, a decision is made in state 302 whether patient activity is being sensed. Again, this determination of state 302 can be made in accordance with the acceleration signal of the sensor 108 exceeding a threshold value in one or more of the x, y, and/or z axes and/or the indication of cyclic acceleration, such as indicating walking. A negative result of decisions of state 302 will result in continued monitoring for onset of patient activity.

A positive result of decision 302 will lead to state 304 wherein the distance value d is set to an initial $d_{n-1}$ value and in this embodiment initialized to zero. From this follows a state 306 wherein the nth components of the distance along the x, y, and z axes is made under the assumption of constant acceleration along the x, y, and z axes respectively as measured by the sensor 108 for the time period, t. In this embodiment, the nth components of the distance along the x, y, and z axes are set equal to the product of the acceleration along the x, y, and z axes respectively times the square of the time period t, each product divided by 2. Thus, the x, y, and z components of the distance is equal to the double integral of the acceleration signal for the time period t, assuming constant acceleration. Again, the exact time interval t is not crucial to the invention, however it is generally preferred that the time period t be selected of a small enough value to correspond generally to a period of constant acceleration with respect to the update frequency of the sensor 108. Following the determination of the x, y, and z components of the distance as determined in state 306 follows a state 310 wherein a calculation is made of the nth total distance traveled, $d_n$ equal to the square root of the sum of the squares of the components of the distance along the x, y, and z axes respectively.

Following the determination of the nth distance increment as determined in state 310, a sum is made in state 312 wherein the distance increment of state 310 is added to the previous distance $d_{n-1}$ to calculate a present total distance traveled, $d_n$ in state 312. Following the calculations of state 312, a decision is made in state 314 whether patient activity is ongoing. A negative result of decision 314 would indicate that the patient activity was of a transitory nature and a return would be made to state 302 to await further patient activity.

A positive result of state 314 will result both in a return to the determinations of state 306, 310 and 312 as previously described as well as a continuation to a decision state 316 wherein a determination is made whether a determined time period has elapsed, in this embodiment six minutes. A negative result of decision state 316 will indicate that the patient activity is ongoing but has not yet reached a six minute duration and again a return will be made to state 306, 310 and 312 where the total distance d is stepwise incremented as previously described.

A positive result of decision state 316 will indicate that a total determined period of patient activity, in this embodiment six minutes, has elapsed, and will result in a recordation of the total distanced traveled d in state 320. As previously mentioned, multiple recordation's of the distance traveled d can be made in state 320 in circumstances where patient activity above the threshold value continues for an extended amount of time. It will be understood, that the determination and recordation made in states 220, 320 of the embodiments previously described comprises possibly consecutive non-overlapping periods of time which in these embodiments comprise six minute periods.

Figure 6:
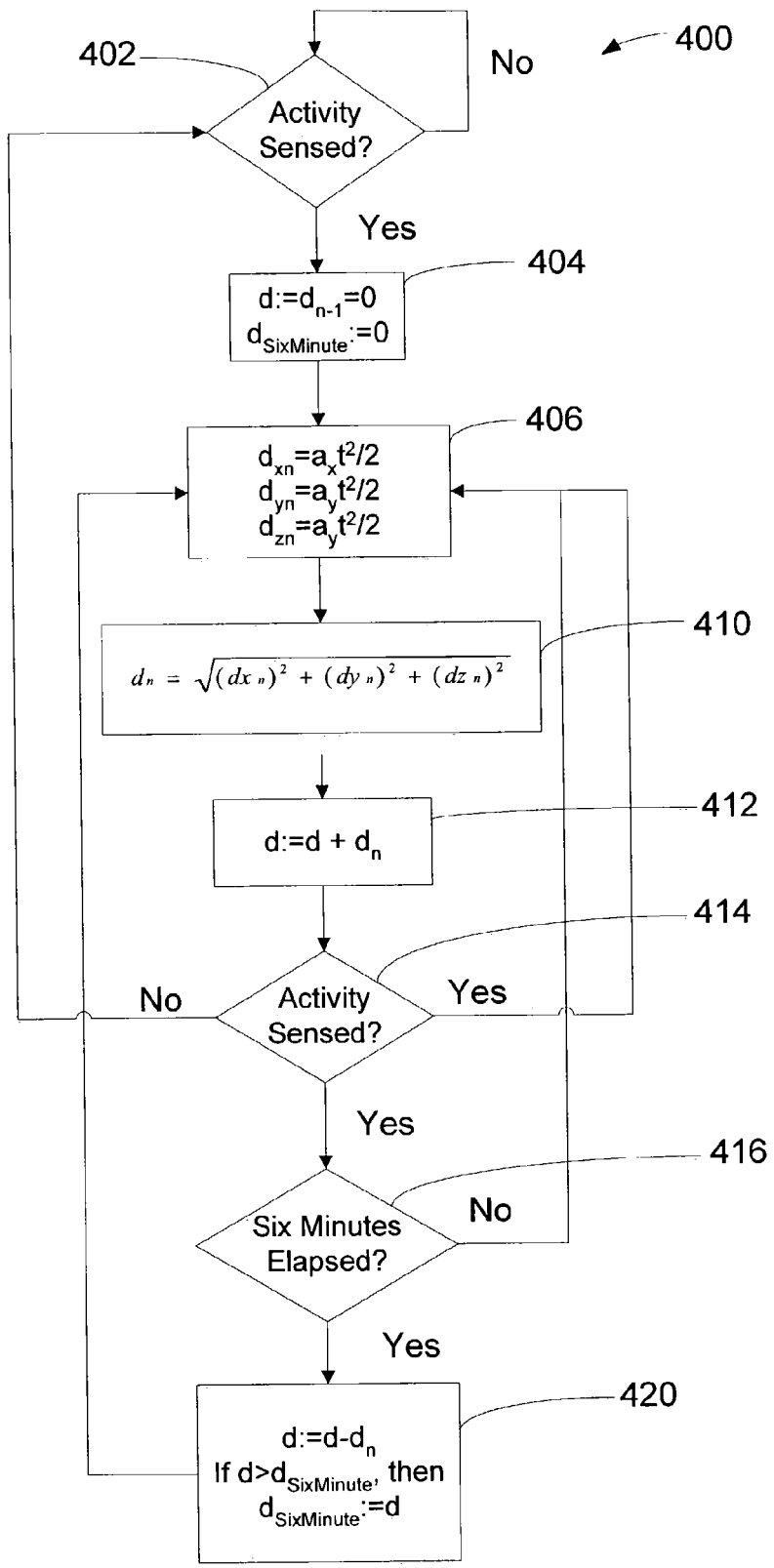
FIG. 6 is a flow chart of another alternative embodiment of a method of automatically determining patient activity suitable for use with the device of FIGS. 2 and 3 where an acceleration signal is provided.

FIG. 6 illustrates an embodiment of the invention similar to that previously described with respect to FIG. 5, however in this embodiment in a variation with provision for a rolling, overlapping evaluation period. In state 402, a determination is made whether patient activity has been sensed in this embodiment substantially similar to those previously described. A positive result of decision state 402 will result in an initialization state 404 wherein a distance value d is set equal to initial $d_{n-1}$ value and in this embodiment set equal to zero as well as an interval distance in this embodiment identified as $d_{six\ minutes}$ which in this embodiment is initialized to zero.

Following this is a state 406 wherein a distance increment is made of a distance along the x, y, and z components as previously described in state 306. This will also be followed by a calculation of a total incremental distance traveled $d_n$ equal to the square root of the sum of the squares of the components of the incremental distance along the x, y, and z axes respectively. An increment will also be made in state 412 substantially similar to that described for state 312 of adding the total distance increment d n calculated in state 410 to the previous distance $d_{n-1}$. This will again lead to a decision state 414 wherein the determination is made whether a patient activity is ongoing or is of a transitory nature as previously described for states 210 and 314. Following the determination of state 414, a determination will be made in state 416 whether a determined period has elapsed which, in this embodiment, is six minutes. Again a negative result of determination of state 416 will result in continued incrementation of the distance as described for states 406, 410, and 412. If the determination of state 416 is positive, the determined period, which in this embodiment is six minutes, and the total distance traveled for the determined six minute period will be calculated and stored as described in state 420.

In state 420, an approximate correction will be made for the additional increment $d_n$ added in state 412 by subtracting from the total distance d the latest increment, $d_n$. Thus, the total distance d will be set equal to the sum of the total distance increments previously added minus the last increment to correspond to a total duration of six minutes. A comparison will then be made to determine whether the total distance d exceeds the previous distance, $d_{six\ minutes}$, for the period indicated in this embodiment. The total distance of the period $d_{six\ minutes}$ was previously set equal to zero and will remain zero until a total period of activity of six minutes has been reached. However, in this embodiment, the provision is made in the calculation and comparison in state 420 for a rolling six minute period for total activity incremented and updated every time period t once six minutes is reached.

The six minute distance is evaluated as indicated as the total distance traveled over any six minute period within what may be a longer period of patient activity and the maximum distance traveled for any six minute period, $d_{six\ minutes}$ is updated if indicated by comparison with the total distance traveled d for the latest six minute period. Thus, in this embodiment, the device 10 automatically evaluates the total distance traveled within any continuous period of patient activity in excess of the determined period which in this embodiment is six minutes and automatically determines and stores the maximum six minute distance traveled observed.

Figure 7:
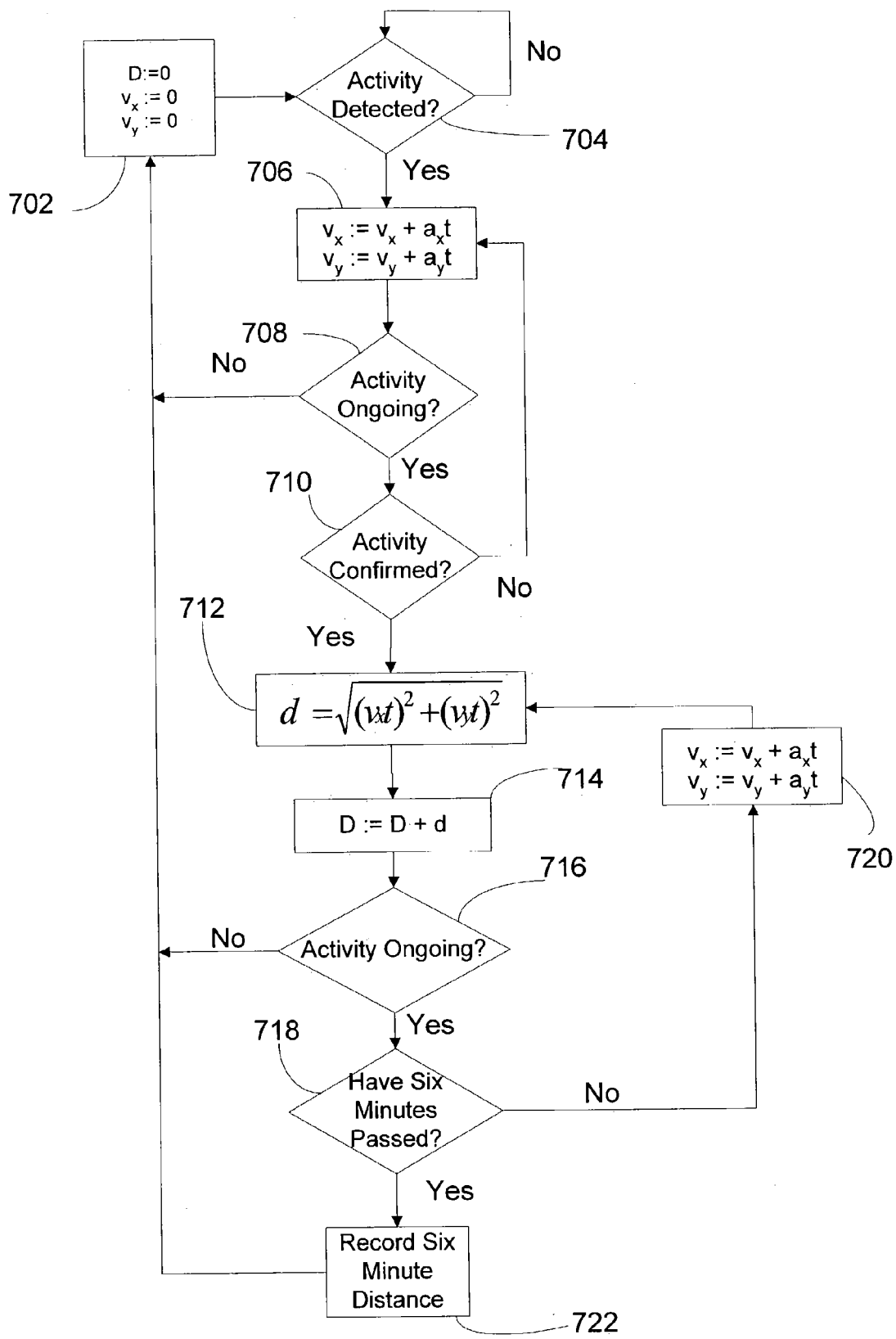
FIG. 7 is a flow chart of another alternative embodiment of a method of automatically determining patient activity suitable for use with the device of FIGS. 2 and 3 where an acceleration signal is provided.

FIG. 7 illustrates another alternative embodiment of the invention adapted for applications where the sensor 108 provides an acceleration signal along x, y, and z axes. In this embodiment, x- and y- acceleration values are iteratively used to update x- and y- velocity values which, in turn, are used to calculate distance traveled, and z- acceleration values are used to indicate continuation of activity. Alternatively, z- acceleration values could additionally be used to update z- velocity values which could, in turn, be included in the distance traveled calculations.

In this embodiment, parameters used to store current velocity and total distance traveled are initialized to zero in initial state 702. State 704 follows wherein sensors monitor the patient for initiation of activity. In this embodiment, sensing of a change in acceleration in the z axis from a zero value to a non-zero value exceeding a predetermined threshold is interpreted as initiation of activity. Alternatively, other indicators of activity initiation, such as described in previous embodiments, could be used. If no activity is sensed, state 704 is continued. Upon sensing activity, the x- and y- acceleration values are stored and state 706 follows.

In state 706, current velocity in the x-y plane is calculated from the previously stored x- and y- acceleration values. Again, velocity in the z-axis could alternatively be used in addition to the x- and y- velocities. Following state 706, after a predetermined period t, is state 708 wherein determination is made whether patient activity is ongoing. The exact time interval t is not crucial to the invention, however it is generally preferred that the time period t be selected of a small enough value to correspond generally to a period of constant acceleration with respect to the update frequency of the sensor 108.

A negative determination of state 708 leads to a return to initial state 702. A positive determination of state 708 leads to state 710 wherein determination is made whether continuous patient activity has persisted for a predetermined period warranting further evaluation. The exact interval used for the predetermined period is not crucial to this invention but, for this embodiment, is one minute.

A negative determination of state 710 indicates that ongoing patient activity has not yet persisted for sufficient duration to warrant further evaluation and leads to a return to state 706 wherein x- and y-velocities are updated with current sensed x- and y- acceleration values. Note that x- and y- acceleration values could be zero, even in the presence of non-zero z- acceleration, indicating that activity is ongoing but that velocity in the x- y- plane has not changed. This would be indicative of a patient walking at a steady pace and would be reflected in the velocity update calculation in state 706 wherein a zero value for x- and/or y- acceleration would leave the corresponding x- and/or y- velocity unchanged.

A positive determination of state 710 indicates that ongoing patient activity has persisted for sufficient duration to warrant further evaluation and leads to state 712 wherein current x- and y- velocity are used to calculate the incremental distance traveled since the last x-, y- velocity update. State 712 is followed by state 714 wherein incremental distance traveled is added to total distance traveled.

State 716 follows state 714, after a predetermined period t, as described above. A determination is made in state 716 whether patient activity is ongoing. A negative determination of state 716 leads to a return to initial state 702. A positive determination of state 716 leads to state 718 wherein a determination is made whether ongoing patient activity has persisted for a predetermined period, in this embodiment, six minutes. A negative determination of state 718, indicating that ongoing patient activity has not yet reached the predetermined period, leads to state 720 wherein x- and y- velocities are updated with current sensed x- and y- acceleration values.

Again, note that x- and y- acceleration values could be zero, even in the presence of non-zero z- acceleration, indicating that activity is ongoing but that velocity in the x-y- plane has not changed. This would be reflected in the velocity update calculation in state 720 wherein a zero value for x- and/or y- acceleration would leave the corresponding x- and/or y- velocity unchanged. Following state 720 is a return to state 712 wherein current x- and y- velocity are used to calculate the incremental distance traveled since the last incremental distance was calculated. The logic described above following state 712 is then repeated for the next time interval t.

A positive determination of state 718 indicates that patient activity has continued for a predetermined period warranting recording of total distance traveled and leads to state 722 wherein total distance traveled is recorded. As previously mentioned, multiple recordings of total distance traveled can be made in state 722 when patient activity continues for an extended period of time. It will be understood that such multiple recordings correspond to possibly consecutive non-overlapping periods of time. Following state 722 is a return to initial state 702 followed by state 704 wherein sensors monitor the patient for initiation or continuation of activity.

Alternatively, the logic described herein could be modified as previously described to make multiple recordings of total distance traveled, when patient activity continues for an extended period of time, wherein such multiple recordings correspond to consecutive, overlapping periods of time.

Figure 8:
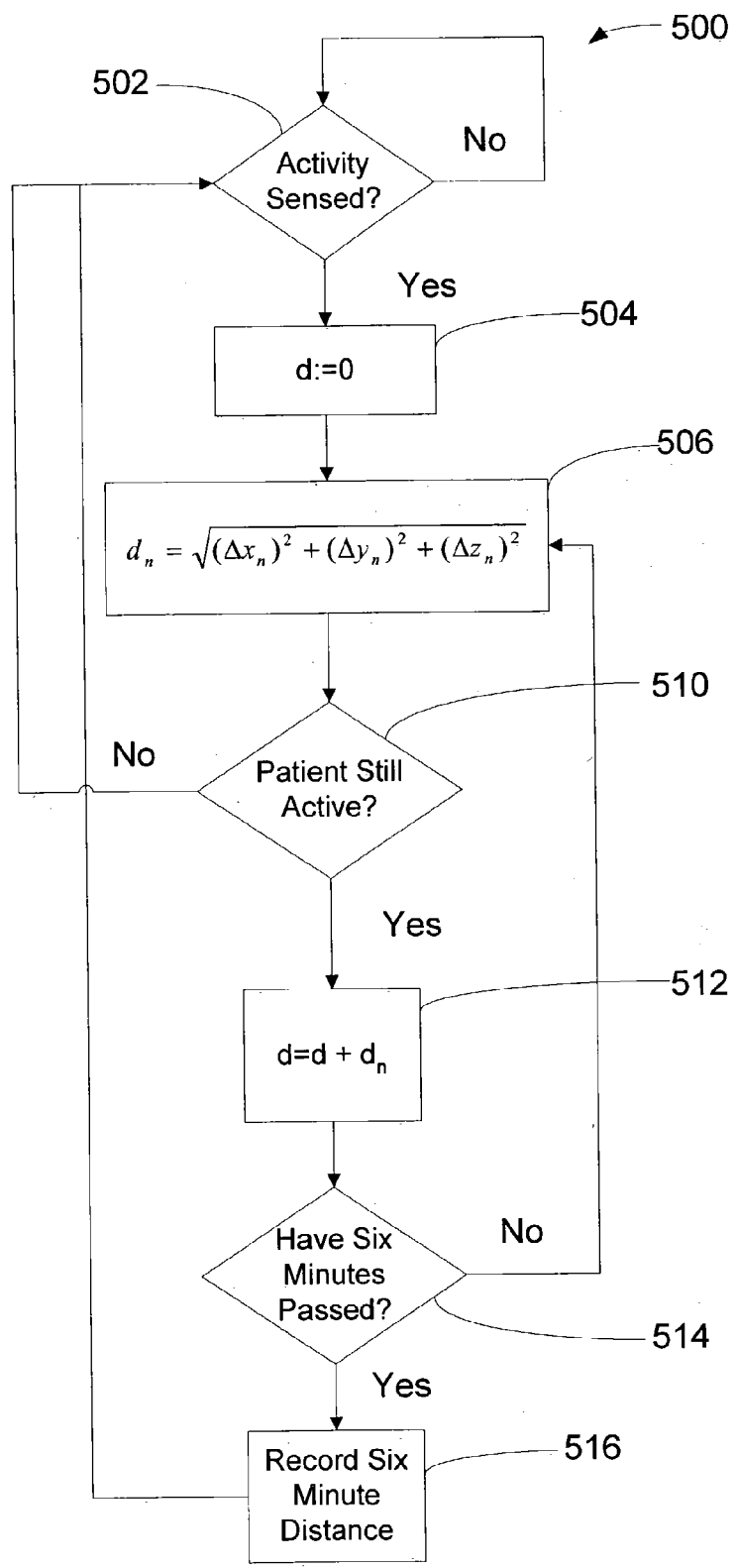
FIG. 8 is a flowchart of an embodiment of a method of automatically determining patient activity suitable for use with the device of FIGS. 2 and 3 where a position signal is provided.

FIG. 8 illustrates an alternative embodiment of the invention adapted for applications where the sensor 108 comprises a direct position sensor, for example a global positioning system (GPS) receiver. In this embodiment, the sensor 108 directly provides position and distance information and thus the calculation of distance from the acceleration signal as previously described for the embodiments of the invention with respect to FIGS. 4–6 is not necessary.

In particular, a decision is still made in state 502 whether patient activity in excess of a determined threshold has been observed. In this embodiment, the evaluation of state 502 can be made on the basis of a change of distance in excess of a determined threshold within a determined period. Alternatively, or in combination, the evaluation of state 502 can be based on the determination of the velocity value in excess of a determined threshold in those applications where the sensor 108 provides velocity as well as position information. Again, a negative result of decision state 502 will result in continued monitoring for an onset of patient activity. A positive result of state 502 will indicate that patient activity in excess of the determined threshold is being observed and analysis of the activity characteristics will be made as follows.

In state 504, a distance value d will be initialized and in this embodiment set equal to zero. Following this an incremental distance will be calculated $d_n$ and in this embodiment is set equal to the square root of the sum of the squares of the change in position along the x, y, and z axes indicated in this embodiment by $\Delta x_n$, $\Delta y_n$, and $\Delta z_n$ respectively. Following the distance increment calculation of state 506, a determination will be made in state 510 whether patient activity is on-going similar to that made in states 210, 314 and 414 as previously described or whether the patient activity was of a temporary nature. An affirmative result of decision state 510 will result in an incrementing of the total distance traveled in state 512 where the distance traveled is set equal to the previous distance traveled plus the distance increment $d_n$ determined in state 506. Following the incrementation of state 512 follows a decision state 514 whether a determined period, which in this embodiment is six minutes, has elapsed. A negative result of this determination will result in a return to state 506 through 512 for further incrementing of the distance traveled, as previously described. A positive result of state 514 will lead to state 516 wherein the total distance d traveled is recorded and a return is made to state 502 for further confirmation of patient activity in excess of the determined threshold.

It is to be understood that the embodiment of the invention described with respect to FIG. 8 is similar to the embodiments described with respect to FIGS. 4 and 5 in that the invention can provide for monitoring and recordation in state 516 of multiple consecutive non-overlapping determined periods, in this embodiment six minutes, in circumstances where patient activity is on-going for multiple six-minute intervals. However, it is to be understood that the aspects of the invention described with respect to FIG. 6, e.g., the rolling determination of a determined interval, can also be employed in embodiments where the sensor 108 provides direct position information such as via a GPS receiver, for example.

While the determination of the total distance traveled d as determined in the increments described in states 506 and 512 have been determined by the device 10, it is certainly envisioned that in certain applications the sensor 108 can provide this information directly and provide a total distance traveled which may be a simple point-to-point linear distance or a step-wise determined distance along the path as described herein.

Figure 9A:
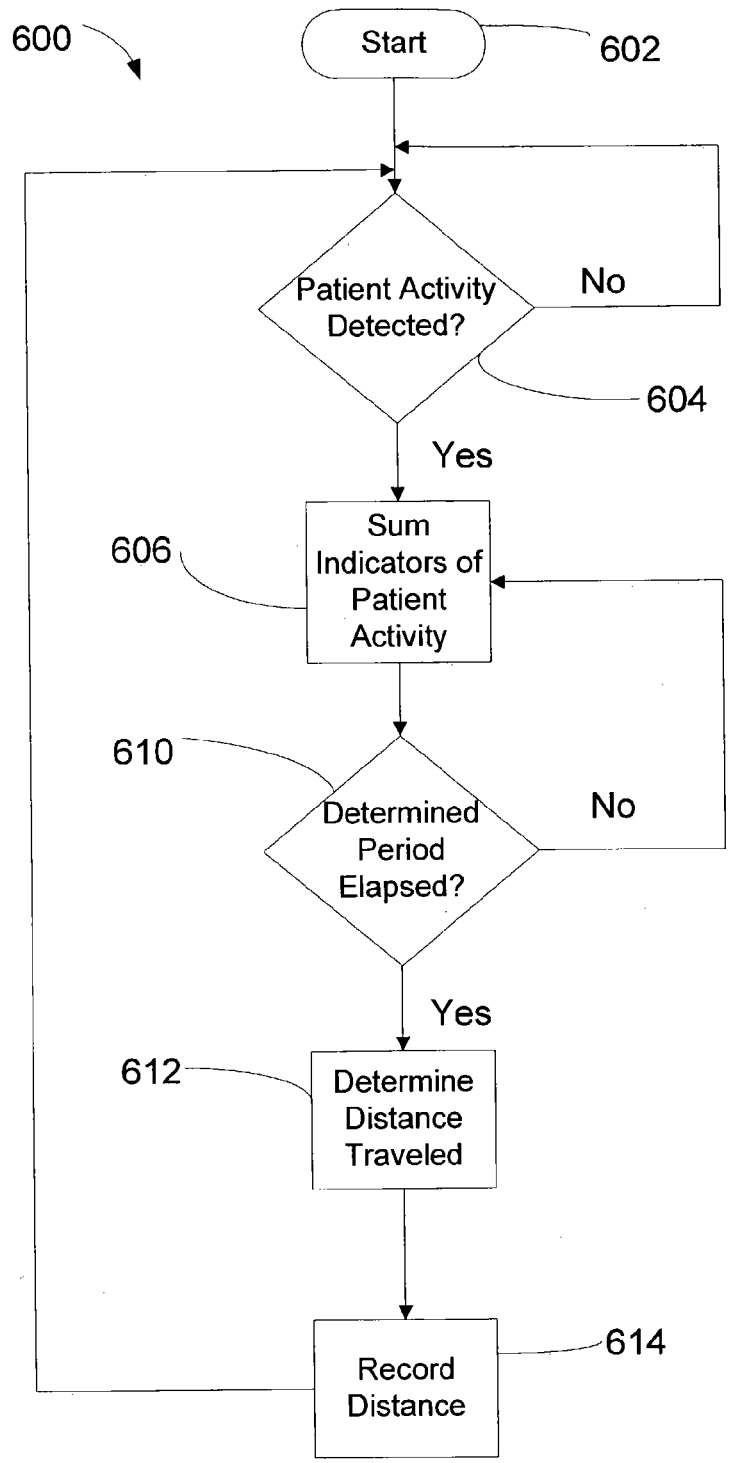
FIG. 9a is a flow chart of an embodiment of a method of quantifying patient activity from a general indicator of patient activity suitable for use with the device of FIGS. 2 and 3.
Figure 9B:
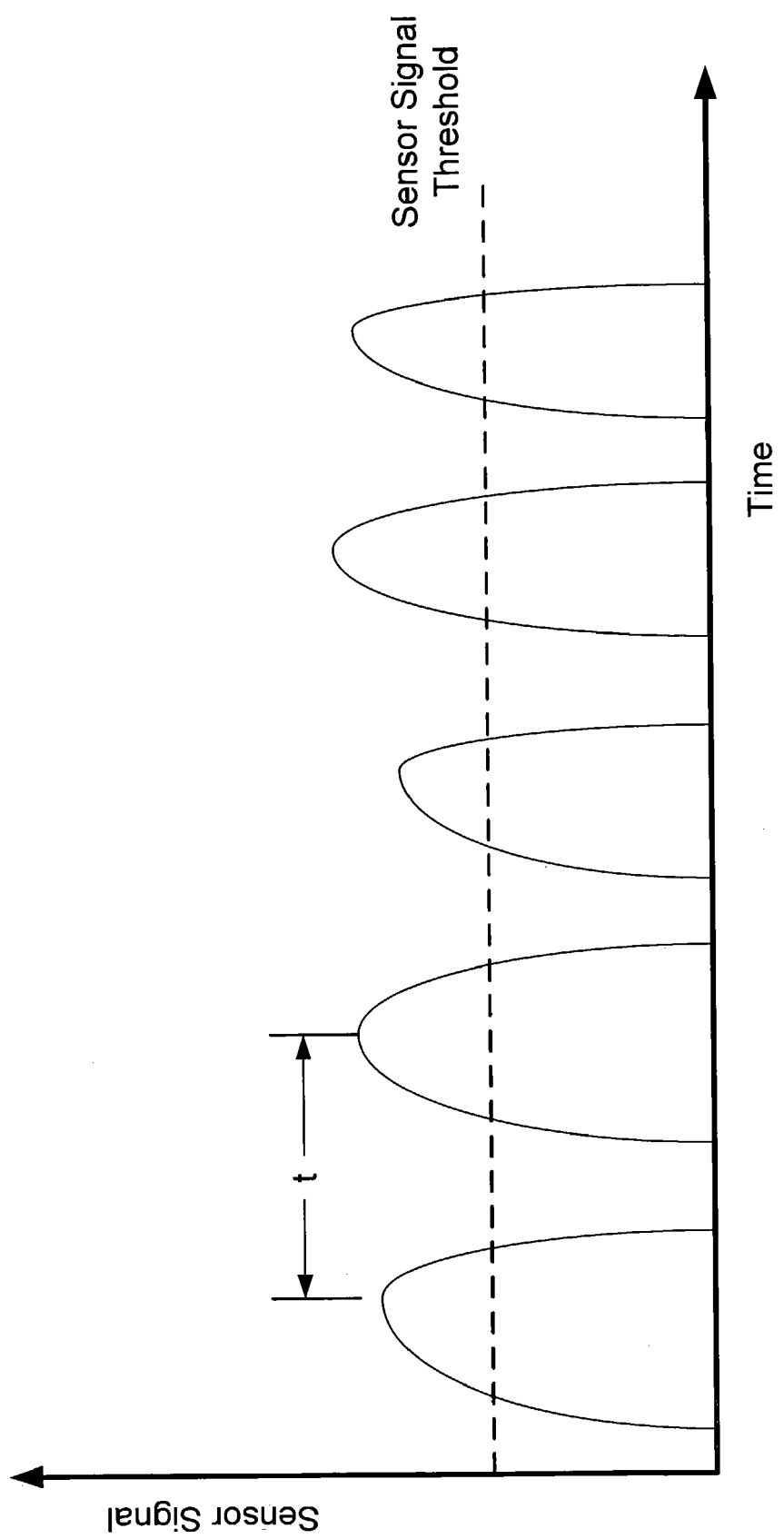
FIG. 9b is a waveform indicating patient activity.

FIG. 9a is a flow chart of another embodiment of a method 600 of determining patient activity wherein a total distance traveled is inferred from an indicator of patient activity. FIG. 9b is a waveform indicating a signal provided by the sensor 108 that can be utilized in the determination shown in FIG. 9a. The signal from the sensor 108 illustrated in FIG. 9b can comprise a simple total acceleration signal that need not be resolved into separate axes. The waveform shown in FIG. 9b indicates a cyclic movement of the patient, such as walking, as indicated by the amplitude of the signal provided by the sensor 108 over time. The waveform shown in FIG. 9b shows five instances of a rising edge of the sensor 108 signal exceeding a sensor signal threshold. These instances of threshold crossing can be used by the device 10 to establish a count of events indicating patient movement in excess of the threshold.

FIG. 9b also indicates a relative timing between the threshold crossing events and also, as indicated in the figure, a time lapse between sensor signal peaks. This time period can be used to determine a rate. The rate and count information may be used individually or in combination to quantify patient activity. For example, a clinical evaluation may be made to determine a distanced walked by the patient in each step and this distance can be multiplied by the event count to approximate a total distance walked during a period of evaluation. The rate information can also be used in a similar manner wherein a walking step rate is correlated to a walking speed, such as in a clinical test. The determined stepping rate can then be multiplied by the corresponding walking speed and by the duration of detected activity to approximate a total distance walked.

The aspects of the invention illustrated in FIG. 9b begin in a start state 602 proceeding to a decision state 604 where a determination is made whether patient activity exceeds a determined threshold. As previously described, the evaluation of state 604 can comprise evaluating whether the sensor 108 signal exceeds a threshold amplitude and/or indicates activity occurring above a determined rate/within a determined period. A negative result of the decision of state 604 results in continued monitoring for onset of patient activity and a positive result of state 604 leads to an evaluation state 606.

In state 606, a calculation is made to determine a distance (equivalent distance) traveled by the patient. In various embodiments, this can comprise counting the number of indications the sensor 108 provides of the patient taking a step, determining the time period between steps, and/or determining a stepping rate. As state 606 proceeds, a decision is also made in state 610 whether the patient activity has continued for a determined period, such as the previously described six-minute period. A negative result of the decision of state 610 results in continued evaluation under state 606.

A positive result of decision 610 results in a calculation in state 612 of the approximate distance traveled by the patient. In various embodiments, the calculation of state 612 can comprise a multiplication of a count established in state 606 by an approximate distance walked per step previously measured, a multiplication of the time period by a walking rate at that step period time a total time, and/or a multiplication of the stepping rate times an average distance per step times total time. It will also be appreciated that the distance determined in state 612 may be an effective distance traveled as the patient may be conducting their activity on a treadmill, stepper, or the like such that no actual displacement takes place or may be walking along a closed path, such as a track, such that they return to their starting location such that no net displacement occurs although a distance around the path is walked.

Following the calculation of state 612, the results of the calculation are stored in memory of the device 10 in a recordation state 614. FIG. 9c shows an embodiment of sample records that can be made in state 614. In the embodiment shown in FIG. 9c, a record is made of the month/day/year of each determination, a value for the maximum step count observed for the determined period, and an equivalent distance traveled. It is to be noted that the record of state 614 can include occurrences where no activity in excess of the threshold was observed which is indicated in this example with the designator N.R.

Following the recordation of state 614, the device 10 returns to the monitoring, calculations, and decisions of states 604–614 as previously described. It will be appreciated that in specific aspects of the invention, the recordation of state 614 can comprise only the greatest distance (equivalent distance) observed or all distances observed. If only the greatest is recorded, the determination can comprise the greatest of separate adjacent periods or a greatest determined period within a longer period of activity as previously described with reference to FIGS. 5 and 6. It will be also appreciated that, in other embodiments, the recordation shown in FIG. 9c may be made on a weekly, monthly, or other periodic basis.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An implantable device for automatically monitoring and reporting patient physical activity, the device comprising:
   at least one implantable sensor operative to provide information related to patient movement;
   a processor in communication with the at least one implantable sensor, wherein the processor is operative to evaluate the information provided by the at least one sensor, automatically determine when the at least one sensor is indicating patient movement in excess of a threshold value, and automatically determine a maximum equivalent quantified activity during a determined interval;
   memory in communication with the sensor to receive and store data related to the patient's movement, including the maximum equivalent quantified activity; and
   a telemetry circuit in communication with the memory and operative to transmit internally determined data related to the patient's activity;
   wherein the sensor comprises an accelerometer; and
   wherein the device double integrates an acceleration signal from the sensor to determine a distance traveled by the patient so as to automatically determine the maximum equivalent quantified activity during the determined interval.

2. An implantable device for automatically monitoring and reporting patient physical activity, the device comprising:
   at least one implantable sensor operative to provide information related to patient movement;
   a processor in communication with the at least one implantable sensor, wherein the processor is operative to evaluate the information provided by the at least one sensor, automatically determine when the at least one sensor is indicating patient movement in excess of a threshold value, and automatically determine a maximum equivalent quantified activity during a determined period;
   memory in communication with the sensor to receive and store data related to the patient's movement, including the maximum equivalent quantified activity; and
   a telemetry circuit in communication with the memory and operative to transmit internally determined data related to the patient's activity;
   wherein determining the maximum equivalent quantified activity during the determined period comprises determining a maximum equivalent distance walked.

3. The device of claim 2, wherein the sensor comprises an accelerometer.

4. The device of claim 2, wherein, when a total episode of patient movement in excess of the threshold value proceeds longer than the determined period, the device continuously evaluates the equivalent quantified activity during all time periods of the determined period within the total episode and determines the largest equivalent quantified activity during any determined period so as to determine the maximum equivalent quantified activity.

5. The device of claim 4, wherein the time periods of the determined period evaluated during the total episode are only non-overlapping periods.

6. The device of claim 2, wherein the sensor comprises a position sensor.

7. The device of claim 6, wherein the position sensor comprises a global positioning system receiver.

8. The device of claim 6, wherein the device determines a distance traveled from an initial position within the determined period to determine the maximum equivalent quantified activity.

9. The device of claim 2, wherein automatically determining when the at least one sensor is indicating patient movement in excess of a threshold value comprises establishing a cyclical acceleration in excess of a threshold value indicative of patient walking.

10. The device of claim 2, wherein automatically determining a maximum equivalent distance walked comprises periodically incrementing an initial distance value with a determined equivalent distance traveled during a measurement period.

11. The device of claim 2, wherein the determined period is selected to correspond to a standard clinical measurement period.

12. The device of claim 2, further comprising:
an implantable stimulation circuit adapted to provide therapeutic electrical stimulation; and
a controller in communication with the at least one sensor and the stimulation circuit such that, upon detection of a cardiac arrhythmia as sensed by the at least one sensor, the controller can induce the stimulation circuit to internally deliver a therapeutic stimulation.

13. A method of automatically determining indices of a patient's physical activity and reporting the same with an implantable device, the method comprising:
internally measuring a parameter indicative of patient movement;
determining whether the measurement of patient movement exceeds a threshold indicating patient movement of sufficient intensity and duration to indicate further evaluation;
calculating an equivalent exertion index for a determined interval;
recording at least one equivalent exertion index; and
providing the at least one equivalent exertion index to an external device;
wherein calculating an equivalent exertion index for a determined interval comprises calculating an equivalent distance walked during the determined interval.

14. The method of claim 13, wherein measuring the parameter indicative of patient movement comprises measuring an acceleration.

15. The method of claim 13, wherein measuring the parameter indicative of patient movement comprises measuring patient position in space with respect to time.

16. The method of claim 13, wherein calculating the equivalent distance walked for the determined interval comprises periodically incrementing the equivalent distance walked over the duration of the determined interval.

17. The method of claim 16, wherein periodically incrementing the equivalent distance walked comprises double integrating an acceleration signal.

18. The method of claim 16, wherein periodically incrementing the equivalent distance walked comprises periodically incrementing the distance by a sensed position signal.

19. The method of claim 16, wherein periodically incrementing the equivalent distance walked comprises periodically updating velocity values to periodically calculate incremental distance walked.

20. The method of claim 13, wherein the determined interval comprises a six minute interval.

21. The method of claim 20, wherein recording the least one equivalent exertion index comprises recording the highest equivalent exertion index calculated during any non-overlapping determined interval within the episode of patient movement exceeding the threshold longer than the determined interval.

22. The method of claim 21, wherein the given period comprises a day.

23. The method of claim 13, wherein recording at least one equivalent exertion index comprises recording the highest equivalent exertion index calculated during any determined interval within an episode of patient movement exceeding the threshold longer than the determined interval.

24. The method of claim 13, wherein recording at least one equivalent exertion index comprises recording the highest exertion index measured during a given period.

25. The method of claim 13, wherein providing the at least one equivalent exertion index to an external device comprises telemetrically transmitting the recorded equivalent exertion index to a physician programmer.

26. A system for automatically monitoring patient physical activity and for evaluating the same, the system comprising:
an implantable device comprising:
means for sensing information related to patient movement;
processing means for evaluating information provided by the sensing means to determine when patient movement in excess of a threshold value is indicated, the processing means further comprising means for determining a maximum equivalent quantified activity during a determined interval; and
data storage means in communication with the processing means for storing data related to the maximum equivalent quantified activity determined over time;
an external device comprising display means for displaying information received from the implantable device; and
means for telemetering data between the implantable device and the external device such that the data stored in the implantable device may be selectively transmitted to the external device for displays
wherein the means for determining a maximum equivalent quantified activity during a determined interval comprises determining a maximum equivalent distance walked.

27. The system of claim 26, wherein the sensing means comprises an accelerometer.

28. The system of claim 26, wherein the external device comprises a physician programmer.

29. The system of claim 26, wherein the implantable device further comprises:
implantable stimulation means adapted to selectively and internally provide therapeutic electrical stimulation; and
control means in communication with the sensing means and the stimulation means such that, upon detection of a cardiac arrhythmia as sensed by the sensing means, the control means can induce the stimulation means to deliver the therapeutic stimulation.

* * * * *